United States Patent [19]

Sato et al.

[11] Patent Number: 4,837,260

[45] Date of Patent: Jun. 6, 1989

[54] CYANOACRYLATE COMPOSITIONS

[75] Inventors: Mitsuyoshi Sato; Takumi Okamura; Kaoru Kimura, all of Nagoya, Japan

[73] Assignee: Toagosei Chemical Industry Co., Ltd., Tokyo, Japan

[21] Appl. No.: 48,894

[22] Filed: May 12, 1987

[30] Foreign Application Priority Data

May 23, 1986 [JP] Japan ............................. 61-117189
Mar. 25, 1987 [JP] Japan ............................. 62-69084

[51] Int. Cl.$^4$ ................................................. C08K 5/24
[52] U.S. Cl. ................................... 524/261; 523/212; 524/377
[58] Field of Search ................. 523/212; 524/261, 377

[56] References Cited

U.S. PATENT DOCUMENTS

| | | | |
|---|---|---|---|
| 2,436,144 | 2/1948 | Howk et al. | 260/37 |
| 2,765,332 | 10/1956 | Coover Jr. et al. | 525/295 |
| 3,178,379 | 4/1965 | Wicker et al. | 525/295 |
| 3,220,960 | 11/1965 | Wichterle | 260/2.5 |
| 3,361,858 | 1/1968 | Wichterle | 264/1 |
| 3,388,199 | 6/1968 | Chaney et al. | 264/182 |
| 3,427,298 | 2/1969 | Tsuboi et al. | 260/91.3 |
| 3,658,749 | 4/1972 | Gordon | 260/37 PC |
| 3,663,501 | 5/1972 | Adams et al. | 523/212 |
| 3,839,065 | 10/1974 | Overhults et al. | 523/212 |
| 3,940,362 | 2/1976 | Overhults | 523/212 |
| 4,105,715 | 8/1978 | Gleave | 156/331 X |
| 4,139,693 | 2/1979 | Schoenberg | 526/297 |
| 4,170,585 | 10/1979 | Motegi et al. | 526/245 |
| 4,171,416 | 10/1979 | Motegi et al. | 526/245 |
| 4,180,913 | 1/1980 | Takeuchi et al. | 438/404 |
| 4,313,865 | 2/1982 | Teranota et al. | 526/278 |
| 4,444,933 | 4/1984 | Columbus | 524/297 |
| 4,477,607 | 10/1984 | Litke | 523/212 |
| 4,533,422 | 8/1985 | Litke | 523/212 |
| 4,550,041 | 10/1985 | Thompson | 428/35 |
| 4,713,405 | 12/1987 | Koga et al. | 523/212 |
| 4,720,513 | 1/1988 | Kameyama et al. | 523/212 |

FOREIGN PATENT DOCUMENTS

| | | |
|---|---|---|
| 53-91995 | 8/1978 | Japan . |
| 53-103092 | 9/1978 | Japan . |
| 0043247 | 4/1979 | Japan . |
| 0034165 | 9/1980 | Japan . |

OTHER PUBLICATIONS

Harris, et al., *J. Polymer Sci.*, A-1, 4, 665-677 (1966).
Haas, et al., *J. Polymer Sci.*, 22, 291 (1956).
L. A. vol.'f, et al., *Khim Volokna*, 2, 14 (1979).
J. Chernikov, et al., *Nauchn Tr., Kuban Gos. Univ.*, 243, 141 (1977).

*Primary Examiner*—Joseph L. Schofer
*Assistant Examiner*—J. M. Reddick
*Attorney, Agent, or Firm*—Wyatt, Gerber, Burke and Badie

[57] ABSTRACT

A cyanoacrylate composition suitable as cyanoacrylate adhesives for bonding porous materials, shaping material and fingerprint detectors comprises a 2-cyanoacrylate as a main component and at least one of crown ethers, polyalkylene oxides and derivatives of the polyalkylene oxides as a curing accelerator and at least one of hydrophobic silicas.

16 Claims, No Drawings

CYANOACRYLATE COMPOSITIONS

BACKGROUND OF THE INVENTION

This invention relates to a cyanoacrylate composition mainly composed of 2-cyanoacrylate. According to this invention, there are provided compositions which can be used as adhesives having rapid setting time, excellent workability and good storage stability for adhesion of various hard-to-bond porous material such as woods, papers, leather, etc., compositions for molding materials reinforced by mixing with glass fibers, polyethylene fibers, etc. and furthermore, compositions useful for detection of fingerprints.

Adhesives comprising cyanoacrylate compositions have been widely used as instantaneous adhesives in industrial fields, medical fields, leisure fields and in general household use because of their property that they readily undergo anionic polymerization due to adsorbed water on the surface of the materials to be bonded, are rapidly cured and their characteristics that they have low viscosity and are free-flowing one-pack type solventless adhesives.

The compositions of this invention can be similarly used as adhesives in these fields. The fields for application thereof are further extended because of rapid curability, workability and stability in bonding of porous materials. In addition, the compositions of this invention may also be used for shaping materials and for detection of fingerprints.

The following two methods have been mainly employed to prevent absorption of adhesives into porous materials when porous materials such as woods, papers, leathers, etc. which are difficult to bond are to be bonded with cyanoacrylate adhesives or to prevent sagging of the adhesives when microgaps are bonded by penetration bonding.

According to one of them, one surface of material to be bonded is pretreated with a primer containing amines which are curing agents and then treated with a cyanoacrylate adhesive, or curing accelerators are previously mixed in the cyanoacrylate adhesive. As the curing accelerators, there are known complexes of imidazoles and $SO_2$ (U.S.Pat. No. 3993678), caffeine, theobromine (U.S. Pat. No. 4042442), polyalkylene oxide and its esters or ethers (Japanese Patent Examined Publication No.37836/85) corresponding to U.S. Pat. No. 4,170,585, crown ethers (Japanese Patent Examined Publication No.2238/80) corresponding to U.S. Pat. No. 4,171,416, podant compounds (U.S. Pat. No. 4386193), normal or acid salts of amines or imines (Japanese Patent Unexamined Publication No.141827/79), alcohols, alcohol ester derivative compounds (Japanese Patent Unexamined Publication No.12166/80), polyethylene glycol dimethacrylic esters (Japanese Patent Unexamined Publication No.200469/82), $SO_3$ complexes of tertiary amines, sulfonium tetrafluoroborate (Japanese Patent Unexamined Publication No.87170/83), polyethylene/propylene oxide monoacrylate, etc. (Japanese Patent Examined Publication No.26513/85), compounds obtained by the reaction of siloxane, phosphoric acid, dicarboxylic acids or their acid chloride, acid anhydride, etc. with diols (Japanese Patent Unexamined Publication No.90277/85), calixarene (Japanese Patent Unexamined Publication No.179482/85), etc.

According to another method, the adhesives are made highly viscous using thickening agents such as polymethyl methacrylate, acrylic rubbers and the like to inhibit absorption of the adhesives into the porous materials. Adhesives of high viscosity which have thixotropic properties are preferred and so, thickening agents which impart thixotropic properties have also been studied and use of fumed silica has been proposed (U.S. Pat. No. 4477607).

When porous materials such as woods, papers, leathers, etc. are bonded by the above two methods, there are the following problems, which hinder further extension of scope of application of cyanoacrylate adhesives.

When curing agents are used and when they are used as primers, an operation of pretreatment of the surface to be bonded is required and this negates the important characteristic of one-pack curing of cyanoacrylate adhesives. Thus, extension of uses cannot be expected, although the instantaneous bonding ability is maintained. Further, inhibition of absorption of adhesives only with addition of curing agent requires a large amount of curing agent, which damages storage stability of adhesives. On the other hand, when a thickening agent is used in order to inhibit the absorption of adhesives into the porous materials, in many cases, it is used in combination with said curing agent to adjust setting time of the adhesives. In this case, when it is attempted to obtain sufficient viscosity, there often occurs stringing, which considerably damages the workability. Fumed silica has been proposed as a thickening agent which causes less stringing and provides thixotropic properties, but use of fumed silica has the problems of separation of components contained in adhesives and settling of fillers. Further, it is difficult to substantially inhibit the absorption of adhesives into porous materials only by increasing the viscosity using a thickening agent. Besides, there occur other problems such as reduction of coatability and bond performance when viscosity is increased. Setting time can be adjusted by joint use of curing accelerators and by increase or decrease of the amount added, but as explained before, with increase of the amount added, storage stability is appreciably reduced.

SUMMARY OF THE INVENTION

The object of this invention is to provide compositions which are useful as cyanoacrylate adhesives, which are free from the above mentioned problems and which have high thixotropic properties, have superior rapid curability and excellent workability in bonding of porous materials and are excellent in storage stability and also useful for other purposes.

DESCRIPTION OF THE INVENTION

As a result of the inventors' intensive researches in an attempt to solve the above mentioned problems, it has been found that use of 2-cyanoacrylate in combination with a specific curing accelerator and a hydrophobic silica overcomes all of the problems.

That is, this invention relates to a cyanoacrylate composition, characterized by containing at least one compound indicated by the following A and at least one compound indicated by the following B.

A: crown ether, polyalkylene oxide and its derivatives.

B: a hydrophobic silica

2-Cyanoacrylates:

2-Cyanoacrylates (2-cyanoacrylic acid esters) are those used as a main component of cyanoacrylate adhesives which have been widely used as instantaneous adhesives. Cyanoacrylate adhesives usually contain additives such as anionic polymerization inhibitors, radical polymerization inhibitors, thickening agents, plasticizers, dyes, pigments and perfumes in addition to 2-cyanoacrylates as a main component. These additives may also be used in the composition of this invention.

As examples of 2-cyanoacrylates, mention may be made of methyl, ethyl, chloroethyl, n-propyl, i-propyl, allyl, propargyl, n-butyl, i-butyl, t-butyl, n-pentyl, n-hexyl, cyclohexyl, phenyl, tetrahydrofurfuryl, heptyl, 2-ethylhexyl, n-octyl, nonyl, oxononyl, decyl, n-dodecyl, ethoxyethyl, 3-methoxybutyl, ethoxyethoxyethyl, trifluoroethyl and hexafluoroisopropyl esters of 2-cyanoacrylic acid.

The anionic polymerization inhibitor which is an additive when the composition of this invention is used as cyanoacrylate adhesives is for inhibition of anionic polymerization of the composition caused by water and the like. Examples thereof are $SO_2$, $SO_3$, NO, $NO_2$, HCl, $H_3PO_4$, acid phosphates, aromatic sulfonic acid, alkylsulfonic acids, propanesultone, trifluoromethanesulfonic acid, perfluoroalkylcarboxylic acids, etc. This anionic polymerization inhibitor is added in an amount of 1–1000 ppm, preferably 5–100 ppm.

The radical polymerization inhibitor is added mainly for inhibiting radical polymerization and anaerobic polymerization which take place with light, etc. during storage. Examples thereof are phenol, cresol, hydroquinone, hydroquinone monomethyl ether, catechol, pyrogallol, etc. Generally, this is added in an amount of 10–10,000 ppm, preferably 100–5000 ppm.

The thickening agent is added for adjusting the viscosity of the adhesive composition and it further has an effect of improving dispersion stability. Examples thereof are polymethyl methacrylate, polymethyl acrylate, polyalkyl-2-cyanoacrylate, acrylic rubber, polyvinyl acetate, polyvinyl ether, cellulose ester, etc. This is added usually in an amount of 1–10% depending on the desired viscosity.

Crown ethers:

The term "Crown ethers" is often used in a broad sense of macroheterocyclic compounds, but in this invention it means macrocyclic polyethers wherein the only hetero-atoms are oxygen. As examples of these ethers, mention may be made of 15-crown-5, 18-crown-6, dibenzo-18-crown-6, benzo-15-crown-5, dibenzo-24-crown-8, dibenzo-30-crown-10, tribenzo-18-crown-6, asym-dibenzo-22-crown-6, dibenzo-14-crown-4, dicyclohexyl-18-crown-6, dicyclohexyl-24-crown-8, cyclohexyl-12-crown-4, 1,2-decalyl-15-crown-5, 1,2-naphtho-15-crown-5, 3,4,5-naphtyl-16-crown-5, 1,2-methylbenzo-18-crown-6, 1,2-methylbenzo-5, 6-methylbenzo-18-crown-6, 1,2-tert-butyl-18-crown-6, 1,2-vinylbenzo-15-crown-5, 1,2-vinylbenzo-18-crown-6, 1,2-tert-butylcyclohexyl-18-crown-6, asym-dibenzo-22-crown-6, 1,2-benzo-1,4-benzo-5-oxygen-20-crown-7, etc.

Polyalkylene oxides:

"Polyalkylene oxides" means polymers which contain, as a main component, one or two or more of compounds such as alkylene oxides, e.g., ethylene oxide, propylene oxide, butylene oxide, trimethylene oxide, tetramethylene oxide (tetrahydrofuran), 1,3-dioxolan, trioxane, tetraoxane, etc. and those of which hydrogen in alkylene group is substituted with a halogen atom, hydroxyl group, phenyl group, etc., such as epichlorohydrin, epibromohydrin, glycidol, styrene oxide, etc. and further include polymers mainly composed of formaldehyde, acetaldehyde, glycerin, etc.

These polymers are required to have a polymerization degree of at least 2, preferably about 4-3000, but naturally, those of 1000 or higher in polymerization degree may also be used, in some cases. Molecular weight of the polymers which is connected with polymerization degree is preferably 400–1,000,000, more preferably 1000–10,000. When polymerization degree is 1 or less (i.e., less molecular weight), the effect of setting time accelerator is small and it is difficult to obtain compositions having thickening effect and thixotropic properties which are desirable in accordance with this invention. When polymerization degree is far more than 10000, namely, molecular weight is larger, compatibility of the polymers with 2-cyanoacrylate tends to decrease and it becomes difficult to produce a homogeneous composition. It is not clear why setting time is accelerated when polymerization degree is 2 or more, but this is considered because oxygen atoms in the chain polyalkylene oxide coordinate with a metal.

Compounds in which the alkylene group has 2-6 carbon atoms, are superior in acceleration of setting time and are preferred for this invention, among which those having ethylene, propylene, isopropylene or tetramethylene groups or combinations thereof are preferred. Especially preferred as those having propylene or tetramethylene or combination thereof.

As examples of polyalkylene oxides used in this invention, the following may be mentioned. Diethylene glycol, triethylene glycol, tetraethylene glycol, polyethylene glycol, polypropylene glycol, poly 1,3-propylene glycol, polytrimethylene oxide, polytetramethylene oxide, polyepichlorohydrin, poly 3,3-bis(-chloromethyl) butylene oxide, polytetramethylene ether glycol, poly 1,3-dioxolan, poly 2,2-bis(-chloromethyl) propylene oxide, ethyleneoxide-propylene oxide block polymer, polyglycerins such as diglycerin, triglycerin, tetraglycerin, etc., formaldehyde condensates, acetaldehyde condensates, trioxane polymers, etc. Furthermore, various polyalkylene oxides sold as polyols for curing polyether type urethanes may also be used in this invention.

Polyalkylene oxide derivatives:

The polyalkylene oxide derivatives used in this invention include typically esters of the above polyalkylene oxides with acids and ethers with hydroxyl group-containing compounds. These are preferred, but this invention is not limited to use of them and those which have a polyalkylene oxide structure in molecule thereof including those which have various substituents at terminals of molecule and those which have other bonding links in polyalkylene oxide can exhibit the effects of this invention. As examples of acids which may constitute the esters, mention may be made of acetic acid, propionic acid, butyric acid, iso-butyric acid, pivalic acid, pentanoic acid, n-hexanoic acid, 2-methylpentanoic acid, t-butylacetic acid, n-heptanoic acid, n-octanoic acid, n-decanoic acid, lauric acid, palmitic acid, stearic acid, oleic acid, cyclohexylcarboxylic acid, cyclopentylcarboxylic acid, cyclopropylcarboxylic acid, acrylic acid, methacrylic acid, maleic acid, itaconic acid, napthhenic acid, benzoic acid, β-naphthylcarboxylic acid, p-toluenecarboxylic acid, furancarboxylic acid, p-chlorobenzoic acid, monochloroacetic acid, cyanoacetic acid, glycolic acid, lactic acid, phenyloxypropionic acid, succinic acid, glutaric acid, adipic acid, sebacic acid, butanetetracarboxylic acid, aconitic acid, propane-1,2,3-tricarboxylic acid, citric acid, ortho-phthalic acid, iso-phthalic acid, trimellitic acid, etc. As examples of the hydroxyl group-containing compounds which may constitute the ethers, mention may be made of methanol, ethanol, propanol, isopropanol, butanol, iso-butanol, hexanol, cyclohexanol, 2-ethyl octanol, decanol, lauryl alcohol, cetyl alcohol, stearyl alcohol, oleyl alcohol, phenol, α-naphthol, β-naphthol, cresol, t-butyl phenol, octyl phenol, nonyl phenol, p-chlorophenol, resol, bisphenol A, 2-chloroethanol, ethylene cyanohydrin, trifluoroethanol, benzyl alcohol, 1,4-butanediol, 1,6-hexanediol, glycerin, sorbitol, hydrogenated bisphenol A, trimethylolpropane, etc.

As examples of the esters and ethers as the polyalkylene oxide derivatives, mention may be made of diethylene glycol monoalkyl ethers (e.g., methyl, ethyl, propyl, butyl, etc. as the alkyl), diethylene glycol dialkyl ethers (e.g., methyl, ethyl, propyl, butyl, etc. as the alkyl), polyethylene glycol monoalkyl ethers (e.g., methyl, ethyl, propyl, lauryl, cetyl, stearyl, oleyl, etc. as the alkyl), polypropylene glycol monoalkyl ethers (e.g., methyl, ethyl, lauryl, propyl, stearyl, cetyl, oleyl, perfluoroalkyl, etc. as the alkyl), polyethylene glycol monoaryl ethers (e.g., octylphenyl, nonylphenyl, etc. as the aryl), polyethylene glycol dialkyl ethers, polyethylene glycol monoalkyl esters (e.g., acetates trifluoroacetates, laurates, stearates, oleates, methacrylates, etc.), polyethylene glycol diesters, polypropylene glycol diesters, bisphenol A-polyalkylene oxide adducts (e.g., ethylene, propylene, etc as the alkylene, the same being applied to the following adducts), hydrogenated bisphenol A-polyalkylene oxide adducts, trimethylolpropane-polyalkylene oxide adducts, glycerine-polyalkylene oxide adducts, polyoxyethylene sorbitan ester, tetraoleic acid-polyoxyethylenesorbitol, adipic acid-polyalkylene oxide adducts, trimellitic acid-polyalkylene oxide adducts, isocyanate compounds-polyalkylene oxide adducts, phosphoric acid-polyalkylene oxide adducts, silica acid-polyalkylene oxide adducts, (polyoxyalkylene) polysilanolates, (polyoxyalkylene) polyesters, (polyoxyalkylene) polyphosphates, etc.

Hydrophobic silica:

The hydrophobic silica used in this invention can be obtained by contacting a hydrophilic silica with a compound capable of reacting with hydroxyl group present on the surface of hydrophilic silica in some form to produce hydrophobic group or a compound capable of being adsorbed onto the surface of hydrophilic silica to form a hydrophobic layer on said surface (these compounds being called "surface treating agent" hereinafter) in the presence or absence of a solvent and preferably, heating them to render hydrophobic the surface of hydrophilic slilica.

As the hydrophilic silica used for production of the hydrophobic silica, there may be used, for example, fumed silica and wet silica, which has preferably 1–100 μm, more preferably 5–50 μm in particle diameter of primary particles. Such particulate silica includes, for example, highly-dispersible amorphous silica obtained by hydrolysis of silicon tetrachloride in oxygen-hydrogen flame. Furthermore, there may also be used alumina-containing silica, titanium oxide-containing silica and iron oxide-containing silica obtained by effecting said hydrolysis in the presence of chlorides such as titanium chloride, aluminium chloride, iron chloride, etc.

As the surface treating agents which convert the surface state of hydrophilic silica to hydrophobic state to produce hydrophobic silica, mention may be made of, for example, hydrophobic group-containing alkyl, aryl and aralkyl silane coupling agents such as n-octyl-trialkoxysilane, etc., silylating agents such as dimethyldichlorosilane, hexamethyldisilazane, etc., silicone oils such as polydimethylsiloxane, higher alcohols such as stearyl alcohol, etc., higher fatty acids such as stearic acid, etc.

In this invention, it is preferred to use hydrophobic silica obtained by surface-treating hydrophilic silica with so-called dimethylsilylating agent or trimethylsilylating agent which can provide dimethylsilyl group or trimethylsilyl group on the surface of hydrophilic silica.

As examples of the dimethylsilylating agents and trimethylsilylating agents, in addition to said dimethyldichlorosilane and hexamethyldisilazane, mention may be made of dimethyldimethoxysilane, dimethyldiethoxysilane, dimethyldiacetoxysilane, dimethylditrifluoroacetoxysilane, hexamethylcyclotrisilazane, trimethylchlorosilane, trimethylbromosilane, N,O-bis(trimethylsilyl)carbonate, N,N-diethylaminotrimethylsilane, N,N-dimethylaminotrimethylsilane, hexamethyldisiloxane, N-trimethylsilylimidazole, bis(trimethylsilyl)acetamide, bis(trimethylsilyl)trifluoroacetamide, bis(trimethylsilyl)urea, 2-trimethylsiloxy-2-pentene-4-one, trimethylsilylacetamide, trimethylsilyl-N,N'-diphenylurea, 3-trimethylsilyl-2-oxazolidinone, bis(trimethylsiloxy)-dimethylsilane, etc.

The hydrophobic silica used in this invention can be obtained by the method mentioned hereabove, but commercially available hydrophobic silica may also be used instead. As commercially available hydrophobic silica, there may be used, for example, AEROSIL R805 (Degussa Co.) surface-treated with n-octyltrimethoxysilane, AEROSIL R202 (Degussa Co.) surface-treated with silicone oil, AEROSIL R972, R974 and R 976 (Degussa Co.) surface-treated with dimethylsilylating agent, AEROSIL R811 and R812 (Degussa Co.) surface-treated with trimethylsilylating agent, etc. These are hydrophobic fumed silicas having a specific surface area of 150±20, 80±20, 110±20, 170±20, 250±25, 150±20 and 200±20 m$^2$/g and a hydrophobic degree of 50, 65, 40, 35, 30, 60 and 60, respectively. As other hydrophobic silica, there is Cab-O-Sil N70-TS (Cabot CO.) which is reported to have a specific surface area of 100±20 m$^2$/g and to be treated with an organosilicone compound.

Mixing ratio:

Mixing ratio of crown ether, polyalkylene oxide and polyalkylene oxide derivative in cyanoacrylate composition may be optionally set within the range in which storage stability is not damaged and setting time is accelerated and depending on the desired viscosity and thixotropic property, but is preferably 0.0001–20 parts by weight, more preferably 0.0005–10 parts by weight of 100 parts by weight of 2-cyanoacrylate. Although it somewhat varies depending on the kind of the compound added, generally, when the amount of the compound is smaller, there are provided less acceleration effect of setting time and less viscosity and thixotropic property. When more than 20 parts by weight, there may occur that dissolution becomes difficult, viscosity of composition becomes too high and the rate of gelation is greatly increased during storage.

Amount of hydrophobic silica to be added may vary depending on particle diameter, hydrophobic degree of silica and kind of the surface treating agent, but is preferably such that ratio of viscosities (thixotropic coefficient) measured at rotation speeds of, for example, 6 rpm and 60 rpm in Brookfield viscometer is more than 2, more preferably more than 3 and especially preferably more than 5. Compositions having optional viscosities can be obtained by changing the amount of hydrophobic silica but preferred amount is 1–30% by weight, more preferably 3–20% by weight of the composition.

The compositions of this invention, are excellent adhesives having suitable viscosity and thixotropic properties and further possessing excellent adhesiveness and especially high bonding speed and excellent storage stability for firmly bonding porous materials such as woods, leathers and papers which have been difficult to bond with conventional 2-cyanoacrylate adhesives with remarkable workability and at high bonding speed. Further, the composition of this invention can provide adhesives free from the problems of gelation during storage and increase of stringing which have been encountered in the conventional adhesives of this kind.

The mechanism of how such action is exhibited is not known. As mentioned above, many curing accelerators and thickening agents for 2-cyanoacrylate adhesives have been known, but the excellent action of this invention can be exhibited only by combination of specific ones, namely, combination according to this invention.

Especially, it is clear from comparative examples given hereinafter and U.S. Pat. Nos. 4477607 and 4533422 that high viscosity cyanoacrylate compositions having thixotropic properties cannot be obtained by single use of hydrophonic silica obtained from hydrophilic silica surface-treated with diemthylsilylating agent or trimethylsilylating agent. Thus, the action exhibited by compositions according to this invention could not have been predicted.

COMPARATIVE EXAMPLES 1–3

Three compositions were prepared which contained 15-crown-5, 18-crown-6 or polyethylene glycol #400 of this invention and other additives in the amounts as shown in Table 1.

The addition amount in ppm of stabilizer and component A (crown ether, etc.) in the following tables is based on the amount of 2-cyanoacrylate. Each setting time of these compositions for beeches in an atmosphere of 23° C. and 60%RH was measured according to JIS K6861 and the results are shown in Table 1. As is clear therefrom, these were 30 seconds for all compositions. Separately, these compositions were placed in sealed vessels of polyethylene and heated at 60° C. for 10 days. Then, each setting time of these compositions for two small pieces of beechwood adhered together and stringing property thereof were measured. As is clear from Table 1, setting time was 45 seconds, 45 seconds, and 60 seconds, respectively and stringings were 10 cm, 10 cm and 20 cm, respectively.

COMPARATIVE EXAMPLE 4–7

Four compositions were prepared which contained AEROSIL R972, AEROSIL R805 or AEROSIL R202 as hydrophobic silica according to this invention and other additives in the amounts as shown in Table 1. In the same manner as in Comparative Examples 1–3, setting time of these compositions for beechwood and stringing property thereof were measured and the results are shown in Table 1.

EXAMPLES 1–4

Four compositions were prepared which contained 15-crown-5 and AEROSIL R972, AEROSIL R805, AEROSIL R202 or Cab-O-Sil N70-TS and other additives in the amounts as shown in Table 1. Each setting time of these compositions for beechwood was measured in the same manner as in the above comparative examples to obtain 20 seconds, 15 seconds, 15 seconds and 15 seconds, respectively. Furthermore, as in the comparative examples, the compositions were heated at 60° C. for 10 days and setting time of the compositions for beechwood and stringing property thereof were measured to obtain 30 seconds, 20 seconds, 20 seconds and 20 seconds, respectively for setting time and 1 cm, 0 cm, 0 cm and 0 cm, respectively for stringing. Thus, no problems were found.

EXAMPLES 5–9

Five compositions were prepared which contained AEROSIL R972 as hydrophobic silica and 18-crown-6 or the like and other additives in the amounts as shown in Table 1. These compositions were subjected to the same tests as in the comparative examples to find some delay in setting time and some increase in stringing, but these were such that caused no special problems.

TABLE 1

| | Composition | | | | | Setting time | Stability (60° C., 10 days) | |
|---|---|---|---|---|---|---|---|---|
| | 2-Cyanoacrylate (part by weight) | Thickening agent (part by weight) | Stabilizer (ppm) | Crown ether, etc. (ppm) | Hydrophobic silica (part by weight) | (Beechwood/Beechwood) | Setting time | Stringing |
| Comparative Example 1 | Ethyl 2-cyanoacrylate (97) | PMMA (3) | SO$_2$ (40) HQ (1000) | 15-Crown-5 (100) | none | 30 sec | 45 sec | 10 cm |
| Comparative Example 2 | Ethyl 2-cyanoacrylate (97) | PMMA (3) | SO$_2$ (40) HQ (1000) | 18-Crown-6 (100) | none | 30 sec | 45 sec | 10 cm |
| Comparative Example 3 | Ethyl 2-cyanoacrylate (97) | PMMA (3) | SO$_2$ (40) HQ (1000) | PEG#400 (1000) | none | 30 sec | 60 sec | 20 cm |
| Comparative Example 4 | Ethyl 2-cyanoacrylate (87.3) | PMMA (2.7) | SO$_2$ (40) HQ (1000) | none | AEROSIL R972 (10) | >180 sec | >180 sec | 1 cm |
| Comparative Example 5 | Ethyl 2-cyanoacrylate (92.15) | PMMA (2.85) | SO$_2$ (40) HQ (1000) | none | AEROSIL R805 (5) | >180 sec | >180 sec | 0 cm |
| Comparative Example 6 | Ethyl 2-cyanoacrylate (92.15) | PMMA (2.85) | SO$_2$ (40) HQ (1000) | none | AEROSIL R202 (5) | >180 sec | >180 sec | 0 cm |
| Comparative Example 7 | Ethyl 2-cyanoacrylate (92.15)* | PMMA (2.85) | SO$_2$ (40) HQ (1000) | none | AEROSIL R202 (5) | 60 sec | 90 sec | 10 cm |
| Example 1 | Ethyl 2-cyanoacrylate (87.3) | PMMA (2.7) | SO$_2$ (40) HQ (1000) | 15-Crown-5 (100) | AEROSIL R972 (10) | 20 sec | 30 sec | 1 cm |
| Example 2 | Ethyl 2-cyanoacrylate (92.15) | PMMA (2.85) | SO$_2$ (40) HQ (1000) | 15-Crown-5 (100) | AEROSIL R805 (5) | 15 sec | 20 sec | 0 cm |
| Example 3 | Ethyl 2-cyanoacrylate (92.15) | PMMA (2.85) | SO$_2$ (40) HQ (1000) | 15-Crown-5 (100) | AEROSIL R202 (5) | 15 sec | 20 sec | 0 cm |

TABLE 1-continued

| | Composition | | | | | Setting time | Stability (60° C., 10 days) | |
|---|---|---|---|---|---|---|---|---|
| | 2-Cyanoacrylate (part by weight) | Thickening agent (part by weight) | Stabilizer (ppm) | Crown ether, etc. (ppm) | Hydrophobic silica (part by weight) | (Beechwood/ Beechwood) | Setting time | Stringing |
| Example 4 | Ethyl 2-cyano-acrylate (92.15) | PMMA (2.85) | SO₂ (40) HQ (1000) | 15-Crown-5 (100) | Cab-O-Sil N70-TS (5) | 15 sec | 20 sec | 0 cm |
| Example 5 | Ethyl 2-cyano-acrylate (87.3) | PMMA (2.7) | SO₂ (40) HQ (1000) | 18-Crown-6 (100) | AEROSIL R972 (10) | 20 sec | 30 sec | 1 cm |
| Example 6 | Ethyl 2-cyano-acrylate (87.3) | PMMA (2.7) | SO₂ (40) HQ (1000) | PEG#400 (1000) | AEROSIL R972 (10) | 20 sec | 30 sec | 1 cm |
| Example 7 | Ethyl 2-cyano-acrylate (87.3) | PMMA (2.7) | SO₂ (40) HQ (1000) | Polyoxyethylene monostearate (2000) | AEROSIL R972 (10) | 30 sec | 45 sec | 2 cm |
| Example 8 | Ethyl 2-cyano-acrylate (87.3) | PMMA (2.7) | SO₂ (40) HQ (1000) | Polyoxyethylene dimethacrylate (5000) | AEROSIL R972 (10) | 30 sec | 45 sec | 3 cm |
| Example 9 | Ethyl 2-cyano-acrylate (87.3) | PMMA (2.7) | SO₂ (40) HQ (1000) | Polypropylene glycol (5000) | AEROSIL R972 (10) | 45 sec | 60 sec | 3 cm |

*5000 ppm of dimethylsilane-17-crown-6 was added

EXAMPLES 10-22 AND COMPARATIVE EXAMPLES 8-9

Compositions were prepared by mixing with stirring the components at the ratio as shown in Table 2 and performances of the compositions as adhesives were measured. The results are shown in Table 2.

The properties shown in Table 2 were measured by the following methods.

Viscosity:

Viscosity was measured by brookfield viscometer BL type with rotor No. 4 and at 6 RPM and 60 RPM or B8H type with rotor No. 7 and at 5 RPM and 50 RPM at 25° C.

Thixotropic index (T.I.) was calculated by the following equation.

$$T.I. = \frac{\text{Viscosity (cps. 6 RPM or 5 RPM)}}{\text{Viscosity (cps. 60 RPM or 50 RPM)}}$$

Bonding speed:

Setting time for hard PVC and beech woods at 23° C. and 60% RH was measured according to JIS K6861.

Bonding strength:

Tensile bond strength for hard PVC at 23° C. and 60% RH was measured according to JIS K6861.

Stability test:

3 g of the adhesive was charged in an aluminum tube and subjected to heating test of 70° C.×7 days to examine thickening, gelation and stringing.

TABLE 2

| | 2-Cyano-acrylate (wt %) | Thickening agent (wt %) | Stabilizer (ppm) | Hydrophobic silica (wt %) | Crown ether, etc. (ppm) | Viscosity (cps) | T.I. | Setting time | Bonding Strength (Kgf/cm²) | Stability |
|---|---|---|---|---|---|---|---|---|---|---|
| Example 10 | Ethyl (89) | PMMA (4) | SO₂ (40) HQ (1000) | AEROSIL R974 (7) | PPG#4000 (5000) | 86,600 | 7.52 | 3 sec (PVC) | 340 | Acceptable |
| Comparative Example 8 | Ethyl (89) | PMMA (4) | SO₂ (40) HQ (1000) | AEROSIL R974 (7) | — | 1,000 | — | — | — | — |
| Example 11 | Ethyl (89.1) | PMMA (4) | SO₂ (40) HQ (1000) | AEROSIL R811 (6.9) | PPG#4000 (5000) | 36,000 | 6.25 | 3 sec (PVC) | 330 | Acceptable |
| Comparative Example 9 | Ethyl (89.1) | PMMA (4) | SO₂ (40) HQ (1000) | AEROSIL R811 (6.9) | — | 7,800 | 4.49 | — | — | — |
| Example 12 | Ethyl (89) | PMMA (4) | SO₂ (40) HQ (1000) | AEROSIL R974 (7) | PTMG#2000 (5000) | 124,000 | 7.31* | 3 sec (PVC) | 360 | Acceptable |
| Example 13 | Ethyl (88) | PMMA (4) | SO₂ (40) HQ (1000) | AEROSIL R811 (8) | PEG#400 (1000) | 44,200 | 5.42 | 3 sec (PVC) 30 sec (beech) | 320 | " |
| Example 14 | Methyl (88) | PMMA (4) | SO₂ (40) HQ (1000) | AEROSIL R972 (8) | PPG/PEG block copolymer (3000) | 125,000 | 7.20* | 3 sec (PVC) 30 sec (beech) | 330 | " |
| Example 15 | Isobutyl (88) | CAB (5) | SO₂ (40) HQ (1000) | AEROSIL R972 (7) | PPG#1000 (5000) | 75,000 | 7.80 | 5 sec (PVC) | 295 | " |
| Example 16 | Ethoxyethyl (86) | CAB (5) | SO₂ (40) HQ (1000) | AEROSIL R972 (9) | PPG#2000/TDI (1/1.5 molar ratio reaction product) (6000) | 187,000 | 8.20* | 5 sec (PVC) | 300 | " |
| Example 17 | Ethyl | PMMA | SO₂ (40) | AEROSIL | PEG#400 | 11,300 | 4.65 | 3 (PVC) | 330 | " |

TABLE 2-continued

| | 2-Cyano-acrylate (wt %) | Thickening agent (wt %) | Stabilizer (ppm) | Hydrophobic silica (wt %) | Crown ether, etc. (ppm) | Viscosity (cps) | T.I. | Setting time | Bonding Strength (Kgf/cm$^2$) | Stability |
|---|---|---|---|---|---|---|---|---|---|---|
| | (89) | (4) | HQ (1000) | R974 (7) | (4600) | | | 20 (Beech) | | |
| Example 18 | Ethyl (89) | PMMA (4) | SO$_2$ (40) HQ (1000) | AEROSIL R974 (7) | PEG#6000 (4600) | 125,000 | 5.92* | 3 (PVC) 20 (Beech) | 350 | " |
| Example 19 | Ethoxyethyl (87) | CAB (5) | SO$_2$ (40) HQ (1000) | AEROSIL R811 (8) | PPG#1000 (4000) PEG monostearate (1000) | 128,800 | 5.67* | 5 (PVC) 30 (Beech) | 300 | " |
| Example 20 | Ethyl (89.5) | PEA (3.5) | PTS (10) HQ (1000) | AEROSIL R810 (7) | PTMG#2000 (2000) PEG#1000 (1000) | 85,000 | 6.20* | 3 (PVC) 20 (Beech) | 340 | " |
| Example 21 | Ethyl/butyl (50/50) (88) | CAB (4) | PTS (10) HQ (1000) | AEROSIL R976 (8) | PTMG#1000 (3000) PEG#600 dimethacrylate (1000) | 175,000 | 7.80* | 3 (PVC) 20 (Beech) | 310 | " |
| Example 22 | Ethyl (90) | PMMA (4) | SO$_2$ (20) HQ (1000) | AEROSIL R974 (6) | PPG#400 (4600) 18-crown-6 0.04 (400) | 13,400 | 5.92 | 3 (PVC) 20 (Beech) | 325 | " |

*Measured at 5 RPM
PMMA: Polymethyl methacrylate, PEA: Polyethylacrylate, CAB: Cellulose acetate butyrate, PEG: Polyethylene glycol, PPG: Polypropylene glycol, PTMG: Polytetramethylene glycol

EXAMPLES 23-31

Eight parts by weight of each surface treating agent as shown in Table 3 was diluted by 12 parts by weight of hexane. Each of the solutions of the surface treating agents in hexane was dropped to 20 parts by weight of fumed silica AEROSIL 200 having surface area of 200 m$^2$/g with stirring. After having been stirred for 30 minutes, each mixture was heated at 110° C. for 1 hour under nitrogen atmosphere to remove hexane and produce a powder. Each resultant powder was put into a flask equipped with a reflux condenser, a stirrer and a thermometer and then was heated with stirring at 250° C. for 4 hours to yield hydrophobic silicas A to G as shown in Table 3.

The hydrophobicity of the resultant hydrophobic silicas was evaluated using their wettings to a solution of water and methanol, which was measured as follows:

Fifty milliliters of distilled water is poured into a 200ml beaker. And after 0.2 gram of hydrophobic silica has been put onto the water in the beaker, methanol is introduced into the water through an outlet of a burette immersed in the water with stirring using a magnetic stirrer. The amount X in milliliter of methanol which has been added until the floating silicas are wetted with the solution of water and methanol, is measured. Then, hydrophobicity is obtained by the following equation:

Hydrophobicity = 100 X / (50+X).

Nine types of adhesives were prepared using hydrophobic silicas A to G in Table 3. The properties of the obtained adhesives are shown in Table 4 together with their formulations.

TABLE 3

A list of hydrophobic silicas prepared in Examples 23-31

| Samples obtained | Silicas to be treated | Surface treating agents (Conc. used, %) | Specific surface area (m$^2$/g) | hydrophobicity |
|---|---|---|---|---|
| A | AEROSIL 200 (product of Japan Aerosil Co.) | Trimethoxyvinylsilane (20) | 166 | 30 |
| B | AEROSIL 200 (product of Japan Aerosil Co.) | Dimethoxymethylvinylsilane (20) | 159 | 35 |
| C | AEROSIL 200 (product of Japan Aerosil Co.) | Divinyltetramethyldisilazane (20) | 147 | 60 |
| D | AEROSIL 200 (product of Japan Aerosil Co.) | Aryltriethoxysilane (20) | 166 | 30 |
| E | AEROSIL 200 (product of Japan Aerosil Co.) | Phenyltrimethoxysilane (20) | 184 | 40 |
| F | AEROSIL 200 (product of Japan Aerosil Co.) | Polymethylphenylsiloxane (20) | 122 | 35 |
| G | AEROSIL 200 (product of Japan | Methyltrimethoxysilane (20) | 157 | 30 |

TABLE 3-continued

| | | A list of hydrophobic silicas prepared in Examples 23–31 | | |
|---|---|---|---|---|
| Samples obtained | Silicas to be treated | Surface treating agents (Conc. used, %) | Specific surface area (m²/g) | hydrophobicity |
| | Aerosil Co.) | | | |

TABLE 4

| | Examples 23–31 | | | | | | | | |
|---|---|---|---|---|---|---|---|---|---|
| | 2-Cyanoacrylate (wt %) | Thickening agent (wt %) | Polymerization inhibitors (ppm) | Hydrophobic silicas (wt %) | Crown ether, etc. (wt %) | Viscosity (Rotor No. 2) | T.I. | Setting time (sec) | Bonding strength (kgf/cm²) | Stability |
| Example 23 | Ethyl (91.5) | PMMA(3) | SO₂(40) HQ(1000) | A(5) | PEG #400 (0.5) | 12000 | 5.1 | 3 | 340 | Acceptable |
| Example 24 | Ethyl (91.5) | PMMA(3) | SO₂(40) HQ(1000) | A(5) | PEG #6000 (0.5) | 58300 | 6.8 | 3 | 360 | " |
| Example 25 | Ethyl (91.5) | PMMA(3) | SO₂(40) HQ(1000) | A(5) | PPG #2000 (0.5) | 53100 | 7.1 | 3 | 360 | " |
| Example 26 | Ethyl (91.5) | PMMA(3) | SO₂(40) HQ(1000) | A(5) | PTMG #2000 (0.5) | 66200 | 7.3 | 5 | 320 | " |
| Example 27 | Methyl (91.5) | PMMA(3) | SO₂(40) HQ(1000) | B(5) | PPG #2000 (0.5) | 51000 | 6.8 | 3 | 340 | " |
| Example 28 | Ethyl (91.5) | PMMA(3) | SO₂(40) HQ(1000) | C(5) | PPG #2000 (0.5) | 48300 | 6.5 | 3 | 340 | " |
| Example 29 | Isobutyl (91.5) | CAB(3) | SO₂(40) HQ(1000) | D(5) | PPG #2000 (0.5) | 55200 | 7.2 | 3 | 330 | " |
| Example 30 | Ethyl (91.5) | PMMA(3) | SO₂(40) HQ(1000) | E(5) | PPG #2000 (0.5) | 46000 | 6.7 | 3 | 320 | " |
| Example 31 | Ethyl (91.5) | PMMA(3) | SO₂(40) HQ(1000) | F(5) | PPG #2000 (0.5) | 52500 | 6.6 | 3 | 320 | " |

The compositions of this invention provide cyanoacrylate adhesives which can easily bond woods, papers, leathers, etc. which have been difficult to bond with cyanoacrylate adhesives. The adhesives obtained in this invention have a high bonding speed, are free from stringing and excellent in storage stability, and thus can be used in both the industrial and household fields. The effects of this invention are remarkable. Furthermore, the compositions of this invention are also excellent as molding agents for fiber reinforced materials and fingerprint detecting agents and thus use of 2-cyanoacrylate can be extended.

What is claimed is:

1. A cyanoacrylate composition which comprises a 2-cyanoacrylate as a main component and at least one of (A) crown ethers, polyalkylene oxides and polyalkylene oxide derivatives and at least one of (B) hydrophobic silicas.

2. A composition according to claim 1 wherein the crown ethers are macrocyclic polyethers where the heteroatoms are oxygen.

3. A composition according to claim 1 wherein the polyalkylene oxides have a polymerization degree of at least 2.

4. A composition according to claim 3 wherein the polyalkylene oxides have a molecular weight of 400–1,000,000.

5. A composition according to claim 1 wherein the alkylene group of the polyalkylene oxide has 2–6 carbon atoms.

6. A composition according to claim 5 wherein said alkylene group is ethylene, propylene, isopropylene, tetramethylene or a combination thereof.

7. A composition according to claim 5 wherein said alkylene group is propylene, tetramethylene or a combination thereof.

8. A composition according to claim 1 wherein the polyalkylene oxide derivatives are esters of the polyalkylene oxide with acids or ethers with hydroxyl group-containing compounds.

9. A composition according to claim 1 wherein the hydrophobic silicas are those obtained by converting the surface of a hydrophilic silica to a hydrophobic surface by treating the surface of the hydrophilic silica with a surface treating agent.

10. A composition according to claim 7 wherein the hydrophilic silica is fumed silica or wet silica.

11. A composition according to claim 9 wherein the surface treating agent is a dimethylsilylating agent or a trimethylsilylating agent.

12. A composition according to claim 1 wherein the amount of component (A) is 0.0001–20 parts by weight for 100 parts by weight of 2-cyanoacrylate.

13. A composition according to claim 1 wherein the amount of component (B) is 1–30% by weight of the composition.

14. A cyanoacrylate adhesive which comprises the composition of claim 1.

15. A cyanoacrylate composition according to claim 12 which additionally contains an anionic polymerization inhibitor, a radical polymerization inhibitor and a thickening agent.

16. A composition for shaping materials which comprises the composition of claim 1.

* * * * *